United States Patent
Nielsen et al.

(10) Patent No.: US 12,378,542 B2
(45) Date of Patent: Aug. 5, 2025

(54) SOLID STABILIZED LACCASE COMPOSITIONS

(71) Applicant: Novozymes A/S, Bagsvaerd (DK)

(72) Inventors: Niels-Viktor Nielsen, Kirke Saaby (DK); Ole Simonsen, Soeborg (DK); Birgitte Andersen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 348 days.

(21) Appl. No.: 17/795,657

(22) PCT Filed: Feb. 4, 2021

(86) PCT No.: PCT/EP2021/052618
§ 371 (c)(1),
(2) Date: Jul. 27, 2022

(87) PCT Pub. No.: WO2021/156342
PCT Pub. Date: Aug. 12, 2021

(65) Prior Publication Data
US 2023/0088815 A1  Mar. 23, 2023

(30) Foreign Application Priority Data

Feb. 4, 2020 (EP) .................................. 20155460
Feb. 6, 2020 (EP) .................................. 20155877

(51) Int. Cl.
*C12N 9/96* (2006.01)
*C12N 9/02* (2006.01)

(52) U.S. Cl.
CPC ............. *C12N 9/96* (2013.01); *C12N 9/0061* (2013.01); *C12Y 110/03002* (2013.01)

(58) Field of Classification Search
None
See application file for complete search history.

(56) References Cited

U.S. PATENT DOCUMENTS 7,960,332 B2 * 6/2011 Simonsen ................ C12N 9/98
510/513
9,578,891 B2 * 2/2017 Marcussen ............. A23K 40/25

FOREIGN PATENT DOCUMENTS

| CN | 1250475 A | 4/2000 |
|---|---|---|
| CN | 109195591 A | 1/2019 |
| EP | 2732018 | 1/2013 |
| WO | 03023142 A1 | 3/2003 |
| WO | 2004067739 A2 | 8/2004 |
| WO | 2006053564 A2 | 5/2006 |
| WO | 2011134809 A1 | 11/2011 |

OTHER PUBLICATIONS

Anonymous, 2014, ip.com. ISSN-1533-0001.

* cited by examiner

*Primary Examiner* — Christian L Fronda
(74) *Attorney, Agent, or Firm* — Eric J. Fechter

(57) ABSTRACT

The invention provides an enzyme granule comprising a mixture of a laccase and a buffer in an amount capable of maintaining an alkaline pH.

18 Claims, No Drawings

SOLID STABILIZED LACCASE COMPOSITIONS

CROSS-REFERENCE TO RELATED APPLICATIONS

This application is a 35 U.S.C. 371 national application of PCT/EP2021/052618, filed Feb. 4, 2021, which claims priority or the benefit from European Patent Application No. 20155460.7, filed Feb. 4, 2020, and European Patent Application No. 20155877.2, filed Feb. 6, 2020. The contents of these applications are fully incorporated herein by reference.

FIELD OF THE INVENTION

The present invention relates to storage stable laccase granules useful in oral care products, which comprises a mixture of a laccase and an alkaline buffer in an amount capable of maintaining an alkaline pH.

BACKGROUND

Laccases are redox enzymes, acting by oxidizing substrates using molecular oxygen. This is different from most other industrial enzymes, which generally belong to the group of hydrolases. While hydrolases are quite specific with respect to substrates, the oxidative nature of laccases results in more unspecific and unpredictable interactions in formulations than hydrolases do, and formulation of laccases may behave differently compared to formulations of hydrolases.

Solid formulations made by granulation are used to stabilize the enzymes and to reduce the amount on enzyme dust released into the environment. WO 2011/134809 discloses granulation of hydrolases for detergents, such as proteases and amylases, and shows that an acidic environment in the granules greatly improves the enzyme stability.

WO 2006/053564 discloses that the residual activity of a granulated laccase is improved by increasing pH of the laccase concentrate used to prepare the granulate. The granulated laccase of WO 2006/053564 does not contain a buffer.

SUMMARY OF THE INVENTION

The present invention provides, in a first aspect, an enzyme granulate, comprising a mixture of a laccase and a buffer, wherein the reserve alkalinity of the granulate is at least 0.3 g NaOH per 100 g granulate.

In an embodiment, the granulate comprises a core and a coating, and the core comprises the laccase and the buffer, or the coating comprises the laccase and the buffer.

Other aspects and embodiments of the invention are apparent from the description and examples.

Unless otherwise indicated, or if it is apparent from the context that something else is meant, all percentages are percentage by weight (% w/w).

DETAILED DESCRIPTION

The laccase activity of laccase granules is generally improved when the laccase is present in an alkaline environment during production. However, we have found that even though pH is increased to establish an alkaline environment during production of such granules, the residual laccase activity will quickly decrease upon storage; even without mixing the granules with other powder ingredients.

Thus, we have found that it is essential to include an alkaline buffer to maintain the alkaline environment after production of the laccase granules. Not only is it necessary to add an alkaline buffer; the buffer must also be added in a surprisingly high amount to maintain laccase activity.

Without being bound by theory, it is believed that without sufficient amount of alkaline buffer, the pH in the micro-environment of the laccase will slowly decrease during storage, which will eventually reduce the laccase activity.

Granule

The granule of the invention comprises a mixture of a laccase and a buffer, wherein the reserve alkalinity of the granulate is at least 0.3 g NaOH per 100 g granulate.

In an embodiment, the buffer has an alkaline pKa; preferably the buffer has a pKa in the range of 8 to 11.

In an embodiment, a 1% w/w aqueous solution/suspension of the granule has an alkaline pH; preferably a pH in the range of 8 to 11; more preferably a pH in the range of 8 to 10.5; and most preferably a pH in the range of 8.5 to 10.5.

The mixture of the laccase and the buffer is a substantially homogenous mixture. More specifically, the laccase and the buffer are not separated, compartmentalized or arranged in discrete layers.

In an embodiment, the granule comprises a core and at least one coating (outer layer) surrounding the core, wherein the core comprises the mixture of laccase and buffer; or the coating comprises the mixture of laccase and buffer.

In another embodiment, the granule comprises
(a) a core, comprising the laccase and the buffer;
(b) a first coating, which is essentially free of the laccase, and
(c) optionally, a second protective coating surrounding the core and first coating.

In another embodiment, the granule comprises
(a) a core, which is essentially free of the laccase;
(b) a first coating comprising the laccase and the buffer, and
(c) a second protective coating surrounding the core and first coating.

Preferably, the first and/or the second coating is a salt, carbohydrate, or polymer coating. Carbohydrates may be sugars, sugar alcohols or starch.

Preferably, the granule is made from ingredients that can be used in foods or food additives.

The granule may be (roughly) spherical.

In an embodiment, the granules has a (weight/volume average) diameter of 100-1500 µm, preferably 250-1200 µm, and more preferably 250-700 µm.

In another embodiment, the granules have a laccase activity of 100-10000 LAMU/g, preferably 200-8000 LAMU/g, more preferably 300-6000 LAMU/g.

Core

The core may comprise the laccase and the buffer. In an embodiment, the core is essentially free of the laccase.

Suitable cores for use in the present invention include, for example, any material suited for layering in fluid bed processes. The core can be insoluble, dispersible or soluble in water. The core material can preferably either disperse in water (disintegrate when hydrated) or solubilize in water by going into a true aqueous solution. Clays (for example, the phyllosilicates bentonite, kaolin, montmorillonite, hectorite, saponite, beidellite, attapulgite, and stevensite), silicates, such as sand (sodium silicate), nonpareils and agglomerated potato starch or flour, or other starch granule sources such as wheat and corn cobs are considered dispersible. Cores can be produced by various methods known in the art, e.g., by granulation.

The cores can be an organic particulate compound e.g. a natural compound such as microcrystalline cellulose, agglomerated or crystalline carbohydrates, e.g. sugars, sugar alcohols (such as mannitol, xylitol, sorbitol, maltitol, isomalt and erythritol), starch, dextrins, flour (e.g. vegetable flour). The material may have been subjected to a steam treatment.

Nonpareils are spherical particles made of a seed crystal that has been built onto and rounded into a spherical shape by binding layers of powder and solute to the seed crystal in a rotating spherical container. Nonpareils are typically made from a combination of a sugar such as sucrose, and a powder such as cornstarch.

In one embodiment of the present teachings the core is a sodium chloride or sodium sulfate crystal (or agglomerated crystals), also referred to as a seed, or other inorganic salt crystal. In another embodiment of the present teachings, the core is a sucrose crystal. Particles composed of inorganic salts and/or sugars and/or small organic molecules may be used as the cores of the present teachings. Suitable water-soluble ingredients for incorporation into cores include: inorganic salts such as sodium chloride, ammonium sulfate, sodium sulfate, magnesium sulfate, zinc sulfate; or urea, citric acid, sugars such as sucrose, lactose and the like.

Cores of the present teachings may further comprise one or more of the following: active agents, polymers, fillers, plasticizers, fibrous materials, extenders and other compounds known to be used in cores.

Suitable polymers include polyvinyl alcohol (PVA), including partially and fully hydrolyzed PVA, polyethylene glycol, polyethylene oxide, polyvinyl pyrrolidine, and carbohydrate polymers (such as starch, amylose, amylopectin, alpha and beta-glucans, pectin, glycogen), including mixtures and derivatives thereof.

Suitable fillers useful in the cores include inert materials used to add bulk and reduce cost, or used for the purpose of adjusting the intended enzyme activity in the finished granule. Examples of such fillers include, but are not limited to, water soluble agents such as salts, sugars and water dispersible agents such as clays, talc, silicates, cellulose and starches, and cellulose and starch derivatives.

Suitable plasticizers useful in the cores of the present teachings are low molecular weight organic compounds and are highly specific to the polymer being plasticized. Examples include, but are not limited to, sugars (such as, glucose, fructose and sucrose), sugar alcohols (such as, glycerol, lower molecular weight polyethylene glycols, sorbitol, xylitol, mannitol and maltitol and other glycols), polar low molecular weight organic compounds, such as urea, or other known plasticizers such as water.

Suitable fibrous materials useful in the cores of the present teachings include, but are not limited to, cellulose, and cellulose derivatives.

In a particularly preferred embodiment, the core essentially consists of sodium chloride, mannitol and/or microcrystalline cellulose.

The core may have an average diameter of 100-1500 µm, preferably 250-1200 µm, and more preferably 250-700 µm.

Preparation of Core

The core can be prepared by crystallization, precipitation, size reduction methods, or by granulating a blend of the ingredients, e.g., by a method comprising granulation techniques such as pan-coating, fluid bed coating, fluid bed agglomeration or granulation, rotary atomization, extrusion, prilling, spheronization, drum granulation, and/or high shear granulation.

Cores without enzyme (laccase) are prepared by the same techniques, but without enzyme.

Methods for preparing the core can be found in, for example, Handbook of Powder Technology; Particle size enlargement by C. E. Capes; Volume 1; 1980; Elsevier. Other useful references include Michael S. Showell (editor); *Powdered detergents;* Surfactant Science Series; 1998; vol. 71; page 140-142; Marcel Dekker; and Martin Rhodes (editor); Principles of Powder Technology; 1990; Chapter 10; John Wiley & Sons.

Coating

The granule may comprise at least one coating. The coating may comprise the laccase and the buffer. In an embodiment, the coating is essentially free of the laccase.

Coating(s) may also be applied to the cores to improve the laccase storage stability, to reduce enzyme dust formation during handling, to improve adherence of a laccase coating onto the core, or for coloring the granule.

The coating(s) may include a salt coating, a carbohydrate coating, and/or a polymer coating. A polymer coating comprises an organic polymer, such as polyethylene glycol (PEG), methyl hydroxy-propyl cellulose (MHPC), or polyvinyl alcohol (PVA). A carbohydrate coating comprises a water-soluble carbohydrate, such as a sugar, dextrin, or sugar alcohol.

Examples of enzyme granules with multiple coatings are shown in WO 93/07263 and WO 97/23606. The coating(s) may also include functional ingredients, such bleach catalysts (e.g. manganese bleach catalysts; MnTACN) and/or bleach activators (e.g. TAED, NOBS).

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In a particular embodiment the thickness of the coating is below 100 µm. In a more particular embodiment the thickness of the coating is below 60 µm. In an even more particular embodiment the total thickness of the coating is below 40 µm.

The coating should encapsulate the core (and the matrix layer) by forming a substantially continuous layer. A substantially continuous layer is to be understood as a coating having few or no holes, so that the core unit it is encapsulating/enclosing has few or none uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

Salt Coating

A salt coating may comprise at least 50% by weight w/w of a salt, e.g., at least 60%, at least 65%, at least 70%, at least 75%, at least 80%, at least 85%, at least 90%, at least 95% or at least 99% by weight w/w.

The salt may be added from a salt solution where the salt is completely dissolved or from a salt suspension wherein the fine particles is less than 50 µm, such as less than 10 µm or less than 5 µm.

The salt coating may comprise a single salt or a mixture of two or more salts. The salt may be water soluble, in particular having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant relative humidity at 20° C. (also referred to as 'humidity fixed point') above 60%, particularly above 70%, above 80% or above 85%, or it may be another hydrate form of such a salt (e.g., anhydrate). The salt coating may be as described in WO 00/01793 or WO 2006/034710.

Specific examples of suitable salts are NaCl ($CH_{20°\ C.}$=76%), $Na_2CO_3$ ($CH_{20°\ C.}$=92%), $NaNO_3$ ($CH_{20°\ C.}$=73%), $Na_2HPO_4$ ($CH_{20°\ C.}$=95%), $Na_3PO_4$ ($CH_{25°\ C.}$=92%), $NH_4Cl$ ($CH_{20°\ C.}$=79.5%), $(NH_4)_2HPO_4$ ($CH_{20°\ C.}$=93.0%), $NH_4H_2PO_4$ ($CH_{20°\ C.}$=93.1%), $(NH_4)_2SO_4$ ($CH_{20°\ C.}$=81.1%), KCl ($CH_{20°\ C.}$=85%), $K_2HPO_4$ ($CH_{20°\ C.}$=92%), $KH_2PO_4$ ($CH_{20°\ C.}$=96.5%), $KNO_3$ ($CH_{20°\ C.}$=93.5%), $Na_2SO_4$ ($CH_{20°\ C.}$=93%), $K_2SO_4$ ($CH_{20°\ C.}$=98%), $KHSO_4$ ($CH_{20°\ C.}$=86%), $MgSO_4$ ($CH_{20°\ C.}$=90%), $ZnSO_4$ ($CH_{20°\ C.}$=90%) and sodium citrate ($CH_{25°\ C.}$=86%). Other examples include $NaH_2PO_4$, $(NH_4)H_2PO_4$, $CuSO_4$, $Mg(NO_3)_2$ and magnesium acetate.

The suitable salts also include the hydrates of these salts.

Preferably the salt is applied as a solution of the salt, e.g., using a fluid bed.

A particularly preferred salt is sodium chloride.

Laccase

The laccase of the invention is any laccase according to enzyme classification EC 1.10.3.2, or a fragment derived therefrom exhibiting laccase activity; or an enzyme exhibiting a similar activity, such as a catechol oxidase (EC 1.10.3.1), an o-aminophenol oxidase (EC 1.10.3.4), or a bilirubin oxidase (EC 1.3.3.5). Preferably, the laccase is an enzyme according to enzyme classification EC 1.10.3.2.

The laccases may be derived from plants, bacteria or fungi (including filamentous fungi and yeasts). Preferably, the laccase is a fungal laccase. The laccase may have a pH optimum below pH 7. Fungal laccases generally have an acidic pH optimum.

Suitable examples of fungal laccases include laccases derivable from a strain of *Aspergillus*, *Neurospora* (e.g., *N. crassa*), *Podospora*, *Botrytis*, *Collybia*, *Fomes*, *Lentinus*, *Pleurotus*, *Trametes* (e.g., *T. villosa*, *T. versicolor*), *Rhizoctonia* (e.g., *R. solani*), *Coprinopsis* (e.g., *C. cinerea*), *Psathyrella*, *Panaeolus*, *Myceliophthora* (e.g., *M. thermophila*), *Schytalidium* (e.g., *S. thermophilum*), *Polyporus* (e.g., *P. pinsitus*), *Phlebia* (e.g., *P. radiata*), or *Coriolus* (e.g., *C. hirsutus*).

Suitable examples of bacterial laccases include laccases derivable from a strain of *Bacillus*.

In a preferred embodiment, the laccase is derived from a strain of *Coprinopsis* or *Myceliophthora*, such as a laccase derived from *Coprinopsis cinerea* (WO 97/08325); or *Myceliophthora thermophila* (WO 95/33836).

Laccase activity can be determined from the oxidation of syringaldazin under aerobic conditions, pH 7.5, 30° C. The violet color produced is measured at 540 nm. One laccase unit (LAMU) is the amount of enzyme that catalyzes the conversion of 1 micromole syringaldazin per minute at these conditions.

Reserve Alkalinity

As used herein, the term "reserve alkalinity" is a measure of the buffering capacity of the granulate composition (gram NaOH per 100 g granulate composition) determined by titrating a 1% (w/v) solution of granulate composition with hydrochloric acid to pH 7.0.

Accordingly, in order to calculate reserve alkalinity as defined herein:

Reserve Alkalinity=$(T \times M \times 40)/(10 \times m)$, where

T=Titer to pH 7.0 (ml)
M=Molarity of HCl (e.g., 0.1 or 0.2 mol/liter)
m=Sample amount of granulate (g)
The value 40 is the molecular weight of NaOH (g/mol)
The value 10 is a conversion factor Dissolve 1.0 g granulate product in deionized water in a 100 ml volumetric flask. Fill up with deionized water to the 100 ml mark. Measure and record the pH and temperature of the sample using a pH meter capable of reading to ±0.01 pH units, with stirring, ensuring temperature is 21° C.+/−2° C. Titrate whilst stirring with 0.1 M or 0.2 M hydrochloric acid until pH measures 7.0. Note the milliliters of hydrochloric acid used. Carry out the calculation described above to calculate the reserve alkalinity to pH 7.0.

The granulate of the invention has a reserve alkalinity of at least 0.30 g NaOH per 100 g granulate. Preferably, the reserve alkalinity is at least 0.35 g NaOH per 100 g granulate; more preferably the reserve alkalinity is at least 0.40 g NaOH per 100 g granulate; even more preferably the reserve alkalinity is at least 0.45 g NaOH per 100 g granulate; and most preferably the reserve alkalinity is at least 0.50 g NaOH per 100 g granulate.

Buffer

One skilled in the art will quickly recognize what type and amount of buffer is needed to achieve the required reserve alkalinity of the granule of the invention.

Many suitable buffers are available to choose from, but the buffer must be capable of maintaining an alkaline pH (an alkaline buffer), as expressed by the reserve alkalinity. Thus, an 1% w/w aqueous solution of the buffer has an alkaline pH; preferably the pH is in the range of 8 to 11, more preferably the pH is in the range of 8.5 to 10.5.

In an embodiment, the buffer has an alkaline pKa, such as a pKa in the range of 8 to 11, more preferably a pKa in the range of 8.5 to 10.5. Examples of suitable buffers include carbonate and many amino acids having alkaline pKa values. Glycine (sodium glycinate) is a preferred buffer.

In a preferred embodiment, the buffer is suitably used in foods and food additives.

Laccase Mediator

The granule of the invention may be used as part of a solid (powder) laccase composition, comprising the granule of the invention, and a laccase mediator.

The laccase mediator acts as an electron donor for the laccase. Thus, the mediator facilitates the electron transfer from the intended substrate to the laccase.

In an embodiment, the laccase mediator can be used in foods or food additives.

In a preferred embodiment, the laccase mediator is chlorogenic acid.

Oral Care Products

An oral care product of the invention comprises the granule and the mediator as described above. Preferably, the amount of the granule is 0.1 to 15% w/w of the oral care product, more preferably the amount of the granule is 0.1 to 10% w/w of the oral care product, or 0.5 to 15% w/w of the oral care product.

In an embodiment, the oral care product comprises the laccase in an amount of 0.5-25 LAMU per oral care product (for example, per tablet, per chewing gum, etc.).

In an embodiment, the oral care product comprises the laccase in an amount of 0.5-25 LAMU/g.

In an embodiment, oral care products are selected from the group consisting of tablets, mints, chewing gums, gels, and toothpastes.

When the granules of the invention are used in oral care products, sugar alcohols and sodium chloride are preferred materials for preparing the granules. They can be used in both the core and coating of the granules. This is because sugar alcohols do not contribute to tooth decay, tastes good and has a low glycemic index. Sodium chloride is extensively used in foods and also tastes good.

Further embodiments of the invention include:

Embodiment 1. An enzyme granule, comprising a mixture of a laccase and a buffer, wherein the reserve alkalinity of the granulate is at least 0.3 g NaOH per 100 g granulate.

Embodiment 2. The granule of embodiment 1, wherein the reserve alkalinity is at least 0.35 g NaOH per 100 g granulate.

Embodiment 3. The granule of embodiment 1, wherein the reserve alkalinity is at least 0.40 g NaOH per 100 g granulate.

Embodiment 4. The granule of embodiment 1, wherein the reserve alkalinity is at least 0.45 g NaOH per 100 g granulate.

Embodiment 5. The granule of embodiment 1, wherein the reserve alkalinity is at least 0.50 g NaOH per 100 g granulate.

Embodiment 6. The granule of any of embodiments 1-5, wherein a 1% w/w aqueous solution/suspension of the granule has an alkaline pH.

Embodiment 7. The granule of any of embodiments 1-5, wherein a 1% w/w aqueous solution/suspension of the granule has a pH in the range from 8 to 11.

Embodiment 8. The granule of any of embodiments 1-5, wherein a 1% w/w aqueous solution/suspension of the granule has a pH in the range from 8 to 10.5.

Embodiment 9. The granule of any of embodiments 1-5, wherein a 1% w/w aqueous solution/suspension of the granule has a pH in the range from 8.5 to 10.5.

Embodiment 10. The granule of any of embodiments 1-9, wherein the buffer has an alkaline pKa.

Embodiment 11. The granule of any of embodiments 1-9, wherein the buffer has a pKa in the range of 8-11.

Embodiment 12. The granule of any of embodiments 1-11, wherein the laccase is an enzyme according to EC 1.10.3.2.

Embodiment 13. The granule of any of embodiments 1-12, wherein the granule is a layered granule comprising a core and a coating.

Embodiment 14. The granule of any of embodiments 1-13, wherein the granule comprises a core and a coating, and the coating comprises the mixture of the laccase and the buffer.

Embodiment 15. The granule of any of embodiments 1-14, wherein the granule comprises a core and a coating, and the core comprises sodium chloride in an amount of at least 50% w/w of the core, and the coating comprises the mixture of the laccase and the buffer.

Embodiment 16. The granule of any of embodiments 1-15, wherein the granule comprises a core and a coating, and the core is essentially free of laccase and comprises sodium chloride in an amount of at least 50% w/w of the core, and the coating comprises the mixture of the laccase and the buffer.

Embodiment 17. The granule of any of embodiments 1-13, wherein the granule comprises a core and a coating, and the core comprises the mixture of the laccase and the buffer.

Embodiment 18. The granule of any of embodiments 1-17, which further comprises an outer salt coating.

Embodiment 19. The granule of any of embodiments 1-17, which further comprises an outer carbohydrate coating.

Embodiment 20. The granule of any of embodiments 1-17, which further comprises an outer polymer coating.

Embodiment 21. The granule of any of embodiments 1-17, which further comprises an outer salt coating comprising sodium chloride in an amount of at least 50% w/w of the coating.

Embodiment 22. The granule of any of embodiments 1-17, which further comprises an outer polymer coating comprising polyethylene glycol, hydroxypropyl methyl cellulose, or polyvinyl alcohol, in an amount of at least 50% w/w of the coating.

Embodiment 23. The granule of any of embodiments 1-17, which further comprises an outer carbohydrate coating comprising sugar, sugar alcohol or dextrin in an amount of at least 50% w/w of the coating.

Embodiment 24. The granule of any of embodiments 1-23, wherein the buffer comprises a carbonate.

Embodiment 25. The granule of any of embodiments 1-23, wherein the buffer comprises a salt of an amino acid.

Embodiment 26. The granule of any of embodiments 1-23, wherein the buffer comprises sodium glycinate.

Embodiment 27. The granule of any of embodiments 1-26, wherein the laccase is a fungal laccase.

Embodiment 28. The granule of any of embodiments 1-27, wherein the laccase has a pH optimum below pH 7.

Embodiment 29. The granule of any of embodiments 1-28, wherein the granule has a laccase activity of 100-10000 LAMU/g.

Embodiment 30. The granule of any of embodiments 1-28, wherein the granule has a laccase activity of 200-8000 LAMU/g.

Embodiment 31. The granule of any of embodiments 1-28, wherein the granule has a laccase activity of 300-6000 LAMU/g.

Embodiment 32. A solid laccase composition, comprising the granule of any of embodiments 1-31, and a laccase mediator.

Embodiment 33. The solid laccase composition of embodiment 32, wherein the laccase mediator is chlorogenic acid.

Embodiment 34. The solid laccase composition of embodiment 32 or 33, which is an oral care product comprising 0.1 to 10% w/w of the granule of any of embodiments 1-31.

Embodiment 35. The solid laccase composition of any of embodiments 32-34, which is an oral care product selected from the group consisting of a tablet, mint, chewing gum, gel, or toothpaste.

Embodiment 36. The solid laccase composition of embodiment 35, which has a laccase activity of 0.5-25 LAMU per oral care product.

Embodiment 37. The solid laccase composition of embodiment 35, which is a tablet, mint, or chewing gum, and which has a laccase activity of 0.5-25 LAMU per tablet, mint, or chewing gum.

Embodiment 38. The solid laccase composition of any of embodiments 32-37, which has a laccase activity of 0.5-25 LAMU/g.

The present invention is further described by the following examples which should not be construed as limiting the scope of the invention.

EXAMPLES

Chemicals were commercial products of at least reagent grade. The laccase used in the examples below is derived from Myceliophthora thermophila, as disclosed in WO 95/33836, SEQ ID NO: 1.

Example 1

A laccase granulate was produced by layered granulation in a Glatt Procell GF3 fluid bed equipped with one 1.2 mm two fluid nozzle in bottom spray configuration. A liquid laccase concentrate (23% dry matter, 5600 LAMU/g) was used in the enzyme feed (Feed 1), which was adjusted to pH 9.4 with 1N NaOH.

The cores for the process was NaCl prepared by sieving Suprasel Fine to 180-300 μm. 2500 g of the NaCl cores was loaded into the fluid bed. Feeds for the granulation were prepared and applied according to Tables 1 and 2. The storage stability of the granulate produced from the granulation is shown in Table 7.

TABLE 1

Granulation components.

| Component | Feed 1 | Feed 2 Outer protective coating |
|---|---|---|
| Laccase concentrate | 1332 g | — |
| Glycine | 2.3 g | — |
| Dextrin Avebe W80 | 46 g | — |
| 1N NaOH to adjust to pH 9.4 | 20 g | — |
| Water | — | 945 g |
| NaCl | — | 315 g |

TABLE 2

Granulation parameters.

| Property | Feed 1 | Feed 2 |
|---|---|---|
| Air inlet temperature, ° C. | 80 | 65 |
| Air flow, kg/h | 120 | 140 |
| Feed rate, g/min | 6-11 | 12-22 |
| Atomization air pressure, bar | 2.0 | 2.0 |
| Product temperature, ° C. | 61-63 | 47-54 |

A granulate with a laccase activity of 1640 LAMU/g was obtained.

Example 2

A laccase granulate was produced by layered granulation in a Glatt Procell GF3 fluid bed equipped with one 1.2 mm two fluid nozzle in bottom spray configuration. A liquid laccase concentrate (23% dry matter, 5600 LAMU/g) was used in the enzyme feed (Feed 1), which was adjusted to pH 9.4 with 1N NaOH.

The cores for the process was NaCl prepared by sieving Suprasel Fine to 200-400 μm. 2000 g of the NaCl cores was loaded into the fluid bed. Feeds for the granulation were prepared and applied according to Tables 3 and 4. The storage stability of the granulate produced from the granulation is shown in Table 7.

TABLE 3

Granulation components.

| Component | Feed 1 | Feed 2 Outer protective coating |
|---|---|---|
| Laccase concentrate | 1143 g | — |
| Glycine | 18 g | — |
| Dextrin Avebe W80 | 45 g | — |
| Water | 1715 g | — |
| 1N NaOH to adjust to pH 9.4 | 150 g | — |
| Water | — | 740 g |
| HPMC | — | 60 g |

TABLE 4

Granulation parameters.

| Property | Feed 1 | Feed 2 |
|---|---|---|
| Air inlet temperature, ° C. | 85 | 85 |
| Air flow, kg/h | 100 | 90 |
| Feed rate, g/min | 9-11 | 12-17 |
| Atomization air pressure, bar | 1.5 | 2.0 |
| Product temperature, ° C. | 56-63 | 80-84 |

A granulate with a laccase activity of 1580 LAMU/g was obtained.

Example 3

A laccase granulate was produced by layered granulation in a Glatt Procell GF3 fluid bed equipped with one 1.2 mm two fluid nozzle in bottom spray configuration. A liquid laccase concentrate (23% dry matter, 5600 LAMU/g) was used in the enzyme feed (Feed 1), which was adjusted to pH 9.4 with 1N NaOH.

The cores for the process was NaCl prepared by sieving Suprasel Fine to 180-500 μm. 3500 g of the NaCl cores was loaded into the fluid bed. Feeds for the granulation were prepared and applied according to Tables 5 and 6. The storage stability of the granulate produced from the granulation is shown in Table 7.

TABLE 5

Granulation components.

| Component | Feed 1 | Feed 2[*] | Feed 3 Outer protective coating |
|---|---|---|---|
| Laccase concentrate | 2165 g | — | — |
| Glycine | 266 g | — | — |
| Dextrin Avebe W80 | 74 g | — | — |
| Water | 656 g | — | — |
| 1N NaOH to adjust to pH 9.4 | 788 g | — | — |
| Water | — | — | 1260 g |
| NaCl | — | — | 420 g |
| Feed 1 | — | 168 g | — |
| Feed 3 | — | 168 g | — |

[*]Feed 2 was prepared as a mix of feed 1 and feed 3 and was applied for a gradual change of the conditions from feed 1 to feed 3.

TABLE 6

Granulation parameters.

| Property | Feed 1 | Feed 2*) | Feed 3 |
|---|---|---|---|
| Air inlet temperature, ° C. | 80 | 75 | 65 |
| Air flow, kg/h | 120 | 130 | 140 |
| Feed rate, g/min | 4-12 | 9-11 | 17-19 |
| Atomization air pressure, bar | 2.0 | 2.0 | 2.0 |
| Product temperature, ° C. | 61-65 | 54-56 | 45-47 |

A granulate with a laccase activity of 2210 LAMU/g was obtained.

Example 4

Residual Laccase Activity After Storage

Reserve alkalinity was measured on the samples above using a 0.2M HCl. Further the stability of the samples was measured by placing closed glasses of the products at 40° C. and 50° C. for one week. Enzymatic activity was measured, and residual activity calculated relative to samples stored at −18° C.

TABLE 7

Residual laccase activity after storage of the laccase granules from Example 1-3.

| | Reserve alkalinity g NaOH/100 g product | Residual activity 40° C.; 1 week | Residual activity 50° C.; 1 week |
|---|---|---|---|
| Example 1 | 0.06 | 89% | 75% |
| Example 2 | 0.08 | 89% | 83% |
| Example 3 | 0.57 | ≥100% | ≥100% |

Based on the data in Table 7, it is clear that laccase stability is improved with increasing reserve alkalinity.

Example 5

Laccase granules were prepared by spraying a laccase concentrate (3650 LAMU/g) onto NaCl cores (ESCO 50291, 130-400 μm) in a Glatt Procell GF3 fluid bed with two different buffers, and without a buffer.

A laccase concentrate was adjusted to pH 10, and two different buffers were prepared and also adjusted to pH 10:

Glycine buffer: 25 g glycine+70 g deionized water+30 g 10N NaOH

Carbonate buffer: 51.5 g $Na_2CO_3$+15.1 g $NaHCO_3$+240 g deionized water 800 g NaCl cores were fluidized in a fluid bed, and Granules A, B and C were prepared by spraying the NaCl cores with three different feeds, prepared by mixing the laccase concentrate with the glycine or the carbonate buffer, and without buffer, as shown in Table 8. Each of the feeds were adjusted to pH 10.0 before spraying the NaCl cores.

TABLE 8

| | Granule A | Granule B | Granule C |
|---|---|---|---|
| Laccase concentrate | 236 g | 242 g | 250 g |
| Glycine buffer | — | 78 g | — |
| Carbonate buffer | — | — | 230 g |
| pH adjusted to | 10.0 | 10.0 | 10.0 |
| Laccase activity | 456 LAMU/g | 375 LAMU/g | 375 LAMU/g |

An accelerated storage stability test was carried out by storing Granules A, B and C in open glasses at 40° C. and 60% RH for 4 weeks. The residual laccase activity after storage is shown in Table 9.

TABLE 9

Reserve alkalinity and residual laccase activity after storage.

| Granule | Reserve alkalinity (g NaOH per 100 g granules) | Residual activity |
|---|---|---|
| A | 0.28 | 20% |
| B | 0.67 | 40% |
| C | 2.26 | 22% |

Table 9 shows that the laccase storage stability is improved by adding an alkaline buffer to the laccase concentrate before preparing the laccase granules.

The reserve alkalinity of Granules A, B and C is also shown in Table 9.

The invention claimed is:

1. An enzyme granule, comprising a mixture of a laccase and a buffer, wherein the reserve alkalinity of the granulate is at least 0.3 g NaOH per 100 g granulate,
   wherein a 1% w/w aqueous solution/suspension of the granule has a pH in the range from 8 to 11; and wherein the laccase is an enzyme according to EC 1.10.3.2.

2. The granule of claim 1, wherein a 1% w/w aqueous solution/suspension of the granule has a pH in the range from 8.5 to 10.5.

3. The granule of claim 1, wherein the granule comprises a core and a coating, and the coating comprises the mixture of the laccase and the buffer.

4. The granule of claim 1, wherein the granule comprises a core and a coating, and the core comprises the mixture of the laccase and the buffer.

5. The granule of claim 1, which further comprises an outer salt coating, carbohydrate coating, and/or polymer coating.

6. The granule of claim 1, which further comprises an outer salt coating comprising sodium chloride in an amount of at least 50% w/w of the coating.

7. The granule of claim 1, which further comprises an outer carbohydrate coating comprising a sugar or sugar alcohol in an amount of at least 50% w/w of the coating.

8. The granule of claim 1, which further comprises an outer polymer coating comprising polyethylene glycol, hydroxypropyl methyl cellulose, or polyvinyl alcohol, in an amount of at least 50% w/w of the coating.

9. The granule of claim 1, wherein the buffer has an alkaline pKa.

10. The granule of claim 1, wherein the buffer comprises a salt of an amino acid, such as sodium glycinate.

11. A solid laccase composition, comprising the granule of claim 1 and a laccase mediator.

12. The solid laccase composition of claim 11, wherein the laccase mediator is chlorogenic acid.

13. The solid laccase composition of claim 11, which is an oral care product comprising 0.1 to 10% w/w of the granule.

14. The solid laccase composition of claim 11, which is a tablet, mint, chewing gum, gel, or toothpaste.

15. The granule of claim 1, wherein the reserve alkalinity of the granulate is at least 0.35 g NaOH per 100 g granulate.

16. The granule of claim 1, wherein the reserve alkalinity of the granulate is at least 0.40 g NaOH per 100 g granulate.

17. The granule of claim 1, wherein the reserve alkalinity of the granulate is at least 0.45 g NaOH per 100 g granulate.

18. The granule of claim 1, wherein the reserve alkalinity of the granulate is at least 0.50 g NaOH per 100 g granulate.

* * * * *